United States Patent [19]

Lo et al.

[11] 4,128,632

[45] Dec. 5, 1978

[54] SOLUBILIZATION OF RAFOXANIDE

[75] Inventors: Pak-Kan A. Lo, Edison; James B. Williams, Freehold, both of N.J.

[73] Assignee: Merck & Co., Inc., Rahway, N.J.

[21] Appl. No.: 876,968

[22] Filed: Feb. 13, 1978

[51] Int. Cl.² ............... A61K 31/79; A61K 31/165
[52] U.S. Cl. ........................................ 424/80; 424/324
[58] Field of Search ................................ 424/324, 80

[56] References Cited
PUBLICATIONS

Nessel – Chem. Abst., vol. 84 (1976), p. 111, 680a.

*Primary Examiner*—Sam Rosen
*Attorney, Agent, or Firm*—David L. Rose; Harry E. Westlake

[57] ABSTRACT

A soluble complex of an insoluble drug, exemplified by Rafoxanide is formed with polyvinylpyrrolidone and water. The complex is formed by combining the insoluble drug and polyvinylpyrrolidone in a suitable water miscible organic solvent, preferably acetone or glycerolformal, and water. The complex is formed in situ. The solvent may be removed, if desired, and the complex remains in aqueous solution. The aqueous solution is then suitable for injection and may be used to treat fasciola or liver fluke infections.

7 Claims, No Drawings

SOLUBILIZATION OF RAFOXANIDE

BACKGROUND OF THE INVENTION

It is known that polyvinylpyrrolidone and Rafoxanide form a water soluble complex, however, there has been no readily available process with which to form such a complex. Rafoxanide is very poorly soluble in water and most organic solvents. Complexes are generally prepared by dissolving both components in a single solvent or a system of solvents, in which the complex is formed, evaporating the solvent or solvents, and dissolving the complex in water. No water-miscible solvent exists in which both Rafoxanide and polyvinylpyrrolidone are soluble. The complex has been formed by dissolving both components in ethyl acetate, forming the complex, spray drying the solution, and dissolving the solid in water. However, this process is slow, expensive, and a large capital investment is required for the spray drying equipment. The instant process is fast and inexpensive and affords a water solution of the Rafoxanide-polyvinylpyrrolidone complex suitable for injection.

SUMMARY OF THE INVENTION

The instant invention is concerned with a process for the preparation of an aqueous solution of a complex of a water insoluble drug and polyvinylpyrrolidone. Thus, it is an object of this invention to describe the process for the preparation of such solution. A further object is to describe the aqueous solution containing such complex. A still further object is to describe the pharmacological uses of this solution. Other objects of this invention will become apparent from a reading of the following description of the invention.

DESCRIPTION OF THE INVENTION

The instant invention is concerned with an aqueous solution of an insoluble drug, specifically Rafoxanide, complexed with polyvinylpyrrolidone. It is known that these two agents will form a complex which is soluble in water. However, because Rafoxanide is very insoluble in water, there has been available no efficient process for the preparation of the complex. The instant process utilizes readily available materials and a minimum number of steps to efficiently and economically prepare the Rafoxanide-polyvinylpyrrolidone complex.

In the first step of this process, the water insoluble drug is partially dissolved in an organic solvent. This solvent should have the characteristics of being miscible with water and also volatile, so that it can be readily removed after the complex is formed, or the solvent should be physiologically acceptable for injection or ingestion. For the drug Rafoxanide the optimum solvents are acetone, which is volatile and may be readily removed when the complex is formed, or glycerolformal, which is physiologically acceptable and may be left in the aqueous solution, for it will not effect the subject into which it is injected or fed. Generally other solvents are unacceptable because of such limited solubility of Rafoxanide, that the complex formation is unacceptably slow, or that the resultant solution has unacceptable viscosity.

The polyvinylpyrrolidone is then dissolved in water independently of the first solution. Polyvinylpyrrolidone is a polymer of vinylpyrrolidone having a molecular weight of between 3,000 and 1 million. The polymer has been employed as an aid in formulating medicinals and cosmetics for considerable periods of time and is considered very non-toxic. It is preferred to employ polyvinylpyrrolidone having a molecular weight of up to about 50,000 since higher molecular weights may make the resultant solution too viscous. Where the resultant soluton is to be employed for injection or infusion, biologically pure grades of polyvinylpyrrolidone, tested to be free of pyrogens and other toxic materials, should be employed. Generally biologically pure grades of polyvinylpyrrolidone with a molecular weight of about 3,000 to 50,000 are employed.

The solubility of Rafoxanide in acetone and glycerolformal is still not such as to allow the instant process to be carried out with total solutions of Rafoxanide. The use of such total solutions would require excess quantities of solvent, and it has been found that the instant process is highly successful when suspensions are employed.

The suspension of Rafoxanide in acetone or glycerolformal is then mixed with the polyvinylpyrrolidone in water. The Rafoxanide is sufficiently soluble in the organic solvent such that when combined with the other solution, formation of the Rafoxanide-polyvinylpyrrolidone complex commences. As the complex, which is water soluble, is formed, it is readily dissolved in the aqueous phase. The removal of the Rafoxide from the organic phase allows more Rafoxide to dissolve which forms still more complex, which dissolves, and the process continues until all of the Rafoxanide has been dissolved and formed the complex with polyvinylpyrrolidone. There results a solution of the complex in water with some organic solvent present.

The solution may be evaporated in order to remove acetone, or the solution may be used as is if glycerolformal is employed.

In practice it is not always necessary to separately prepare solutions of Rafoxanide in the organic solvent and polyvinylpyrrolidone in water. To facilitate the process the materials may be added in any order which is deemed practicable. Often the organic and aqueous solvents are combined and the solid polyvinylpyrrolidone and Rafoxanide added thereto. Or the water may be combined with the polyvinylpyrrolidone and the organic solvent and Rafoxanide added thereto separately. The order of combination of the ingredients is not critical to the operation of this process.

The range of proportions of acetone or glycerolformal to water which may be employed in this process is wide and successful results have been obtained when the complexing solution consists from 10 to 80% organic solvent by volume. The preferred ranges of organic solvent is between 20% and 70% of the total volume.

The proportion of Rafoxanide to organic solvent in the complexing solution is generally maintained from about 10 to 75% and it is preferred to utilize about 15 to 50% (proportions in weight to volume).

The proportion of polyvinylpyrrolidone to water in the complexing solution is from about 25% to 150%. It is preferred to employ from about 30 to 100% (proportions in weight to volume).

The aqueous solution which results when the organic solvent is evaporated may be diluted with water to any desired volume and administered to a patient in need of such medication. This solution is identified as the injectable solution. The solution is acceptable for oral administration as well as injection or infusion, and the administration is carried out using techniques known to those skilled in this art.

In addition, it has been found that for best results the pH of the injectable solution of the complex should be greater than 8, and the optimum pH is 8.4. Thus, sufficient base, such as an alkali metal hydroxide, preferably sodium hydroxide or potassium hydroxide is employed, such that the final pH is at this level.

Also, if it is desired, additional agents which aid in the stability, clarity, or non-foamability of the final solution may be added.

The injectable solution of the rafoxanide, polyvinylpyrrolidone complex contains generally from 5 to 15% of active compound based on the weight of Rafoxanide employed. The preferred solutions contain from about 7.5 to 125 by weight of Rafoxanide. When acetone is used as the organic solvent, it is preferred to prepare a 7.5% solution, by weight, of Rafoxanide. When glycerolformal is employed, it is preferred to prepare a 10% solution, by weight of Rafoxanide.

Rafoxanide is a highly active compound finding utility in the treatment of liver fluke infections in animals. A complete disclosure of the compound and its use may be found in U.S. Pat. No. 3,798,258. Rafoxanide is named chemically as 3'-chloro-4'-(p-chlorophenoxy), 3,5-diiodosalicylanilide. The insolubility of Rafoxanide in water has limited the use of the drug such that injection techniques have not been available to the practitioner. By virtue of the instant invention, it is now possible to utilize Rafoxanide as an aqueous injection thus furthering the ability of the practitioner to combat liver fluke infections.

EXAMPLE 1

A 1 liter solution of the Rafoxanide-polyvinylpyrrolidone complex is prepared which has the following ingredients:

Rafoxanide — 75 g.
Polyvinylpyrrolidone — 225 g.
Sodium hydroxide — 4.7 g.
Benzyl alcohol — 10.0 g.
Water, distilled — q.s. to 1 liter The sodium hydroxide is dissolved in 200 ml. of distilled water and 400 ml. of acetone is added. With agitation, 225 g. of polyvinylpyrrolidone (molecular weight of about 3000) is added followed by 75 g. of Rafoxanide. The mixture is stirred until all of the materials have dissolved (about ½ hour). If necessary, a further portion of distilled water (up to 500 ml.) may be added. The mixture is placed under vacuum at 60° C. and the acetone is removed. When all of the acetone is removed, the benzyl alcohol is added and the mixture diluted to 1 liter with distilled water.

EXAMPLE 2

A 1 liter solution of the Rafoxanide-polyvinylpyrrolidone complex is prepared which has the following ingredients:

Rafoxanide — 100 g.
Polyvinylpyrrolidone — 200 g.
Sodium hydroxide — 6.4 g.
Glycerolformal — 200 g.
Benzyl alcohol — 10 g.
Water, distilled — q.s. to 1 liter The sodium hydroxide (6.4 g.) is dissolved in 600 ml. of water and 200 g. of polyvinylpyrrolidone (molecular weight about 3,000) is added with agitation. With continuing agitation 200 g. of glycerolformal is added followed by 100 g. of Rafoxanide. The mixture is heated to 60° C. and stirred for 1 hour whereupon all of the materials dissolved. The benzyl alcohol is added and the solution allowed to cool to room temperature. The solution is then diluted to 1 liter with distilled water.

What is claimed is:

1. A process for the preparation of an aqueous solution of a Rafoxanide-polyvinylpyrrolidone complex which comprises:
    (a) combining the Rafoxanide and polyvinylpyrrolidone in a mixture of acetone or glycerolformal and water;
    (b) agitating the mixture until a solution is achieved;
    (c) removing the acetone or optionally removing the glycerolformal; and
    (d) if necessary, diluting the solution to the desired volume with water.

2. The process of claim 1 wherein the amount of acetone or glycerolformal employed in the complexing solution is from 10 to 80% of the total volume of the solution obtained in step a).

3. The process of claim 2 wherein the proportion of acetone or glycerolformal is from 20 to 70 of the total volume.

4. The process of claim 1 wherein the weight to volume proportion of Rafoxanide to the acetone or glycerolformal is from 10 to 75%.

5. The process of claim 4 wherein the proportion of Rafoxanide to the acetone or glycerolformal is from 15 to 50%.

6. The process of claim 1 wherein the weight to volume proportions of polyvinylpyrrolidone to water is from 25 to 150%.

7. The process of claim 6 wherein the weight to volume proportion of polyvinylpyrrolidone to water is from 30 to 100%.